(12) United States Patent
St. Germain (10) Patent No.: US 6,520,949 B2
(45) Date of Patent: Feb. 18, 2003

(54) METHOD AND APPARATUS FOR ADMINISTERING FLUID TO ANIMALS SUBCUTANEOUSLY

(76) Inventor: Martin St. Germain, 151 Terry Dr., Slidell, LA (US) 70458

(*) Notice: Subject to any disclaimer, the term of this patent is extended or adjusted under 35 U.S.C. 154(b) by 0 days.

(21) Appl. No.: 09/824,325

(22) Filed: Apr. 2, 2001

(65) Prior Publication Data

US 2002/0177838 A1 Nov. 28, 2002

(51) Int. Cl.[7] .............................................. A61M 31/00
(52) U.S. Cl. ........................... 604/500; 604/29; 604/48; 604/49; 604/93; 604/171; 604/174; 119/96; 119/120
(58) Field of Search .............................. 604/29, 48, 49, 604/93, 171, 174, 175, 500; 119/96, 120

(56) References Cited

U.S. PATENT DOCUMENTS

| | | | |
|---|---|---|---|
| 3,633,585 A | * 1/1972 | McDonald, Jr. | 604/29 |
| 4,496,349 A | * 1/1985 | Cosentino | 604/175 |
| 4,955,890 A | * 9/1990 | Yamamoto et al. | 604/175 |
| 5,057,075 A | * 10/1991 | Moncrief et al. | 604/175 |
| 5,474,534 A | * 12/1995 | Schlitt | 604/500 |
| 5,702,372 A | * 12/1997 | Nelson | 604/524 |
| 5,762,636 A | * 6/1998 | Rupp et al. | 604/175 |
| 5,945,435 A | * 8/1999 | Evetts | 514/330 |

* cited by examiner

Primary Examiner—Robin O. Evans
(74) Attorney, Agent, or Firm—Garvey, Smith, Nehrbass & Doody, L.L.C.; Charles C. Garvey, Jr.

(57) ABSTRACT

A method of administering fluids to an animal such as a pet (dog, cat, etc.) zoo animal, research animal, or exotic animal, includes the initial step of forming one or more openings in the animal's skin, at least one of the openings being preferably positioned proximally on the animal's body. An elongated catheter that includes a wall, a lumen and proximal and distal end portions is then placed into a subcutaneous space that extends proximally to distally on the animal's body. The catheter is preferably provided with a plurality of openings that are preferably positioned distally and through the catheter wall. The proximal portion of the catheter is anchored to the animal's skin externally and at the proximally positioned opening. Fluids are then transmitted to the animal via the catheter by removably connecting a fluids containing vessel to the catheter and then discharging the fluids from the vessel into the subcutaneous space via the catheter. Because the openings are positioned primarily distally on the catheter wall, fluids do not leak out of the incision or opening. The catheter tube is preferably manufactured of a material (silicone) that can remain in place subcutaneously for up to one year.

33 Claims, 6 Drawing Sheets

METHOD AND APPARATUS FOR ADMINISTERING FLUID TO ANIMALS SUBCUTANEOUSLY

BACKGROUND OF THE INVENTION

1. Field of the Invention

The present invention relates to the administration of fluids, as well as medications into the subcutaneous (under the skin) area of a pet or other animal such as a dog, cat, etc. More particularly, the present invention relates to an improved method and apparatus for use in veterinary medical and animal research industries that features an improved catheter construction adapted to be placed subcutaneously, enabling convenient administration of fluids and medications into the animal's body through the subcutaneous route without the use of needles (in one embodiment) by the owner of the animal in the animal's home environment.

2. General Background of the Invention

As veterinary medical technology has improved, pets are living longer, healthier lives. However, as pets become older, a high percentage of them develop chronic kidney disease associated with old age. This disease is debilitating and eventually fatal. There are three important factors in the treatment of this disease. They are: change of diet, control of anemia and phosphorus levels in the blood, and the long term administration of subcutaneous or intravenous fluids. Of these, fluid administration is the most critical. Fluid administration works to increase the perfusion of the kidneys and excretion of uremic toxins. As this excessive fluid is eliminated, it will carry out uremic toxins that the body can no longer eliminate on its own. These factors have been recognized for over 50 years.

Special diets have been developed to restrict protein and the build up of toxic byproducts. Hormones and phosphate binders have been developed that can control the anemia as well as the elevated phosphorus levels. However, fluids are still the most important aspect of the treatment of this disease. Today, fluids are still administered the way they were fifty years ago. If the animal was hospitalized, the fluids would be administered through an I.V. catheter directly into a vein or given by subcutaneous injections with needles by a trained technician. However, once the patient was stabilized and ready to be released, the options were very limited. One option would be for the client to return with the pet every few days to the hospital to have subcutaneous or intravenous fluids administered by trained personnel. The other option would be for the client to be trained to administer the subcutaneous fluids at home using the conventional approach of multiple needle sticks and the injection of large volumes of fluids up to twice daily.

Fluid therapy had to be carried out by the administration of subcutaneous fluids in large volumes through a large-bore needle attached to an intravenous administration set or syringe. The volume of fluid required frequently exceeds 300 ml per day. This is equivalent to 10 ounces of fluids or 100 of the familiar 3 ml syringes used for routine injections. Because of the large volume of fluids being administered, multiple injections must be made up to twice daily. In general, pet owners are very squeamish about injecting drugs and fluids into their pets with needles. Health risk are present as well. It is impossible to sterilize the skin of the patient prior to each stick with the needle so the risk of infection is significant. Besides the pain and risk to the pet, there is risk of the owner sticking themselves with the needle and causing an infection. Disposal of the needles can also create a hazard to humans. Even when the client could tolerate this treatment of their pet, the pet would frequently withdraw and hide and the close relationship with their owner would suffer. Many owners would give up in frustration and the animal would suffer or be euthanized.

This subcutaneous fluid administration procedure and device was developed to address these problems. The combination of materials used, technique of implantation and maintenance, and subtle design characteristics have combined to produce a method and device that fills a glaring need in the treatment of animals with kidney and other chronic diseases. The implanted subcutaneous fluid administration tube can remain implanted for a year or more.

There has never been a usable device available to veterinarians for administration of fluids and medications to pets into the subcutaneous space, other than a hypodermic needle.

The method and apparatus of the present invention will improve the health and well-being of an animal as well as ease the owner's fears about administering home treatment for their pet. It will result in less animals being euthanized for chronic but treatable diseases.

BRIEF SUMMARY OF THE INVENTION

The method and apparatus of the present invention involves passing a specially designed catheter tube, composed of a material suitable for internal animal body use, through a small incision or opening in the skin and than tunneling the tube under the skin until it reaches the animal's flank area.

The catheter tube can be stiffened by an internal stainless steel stylet which allows it to be gently forced through the subcutaneous space.

The catheter tube is generally passed from the neck area all the way to the flank location. Once placed, the stylet is withdrawn. The proximal end of the tube is capped with an injection port fitting, which can be penetrated by and connected to a short hollow plastic needleless injector. This injector can be attached either to an intravenous line and bag of I.V. fluids, or can be attached to a large syringe filled with fluids and/or medications.

Fluids or other medications can thus be administered to the pet by the owner without the need for an injection with a needle into the pet. This device also does not require the owner to handle a hypodermic needle. With the subcutaneous fluid tube technique of the present invention, the animal does not even know treatment is being administered. There are no needle sticks, and the fluids do not cause pain to the patient because they are the same concentration as normal body fluids and therefore not irritating. The fluids run into the patient at a rate of 100 ml (3 ⅓ ounces) per 1 ½ minutes thus making the treatment simple for the owner. Generally, the owner attaches a 1,000 ml fluid bag to a hanger attached to the top of a door. A standard IV administration set attaches the fluids to the implanted subcutaneous fluid administration tube using special needleless connectors. While sitting with the patient in their lap, the treatment can be finished in just 2–3 minutes. The bond and trust between the pet and the owner is not broken.

The present invention meets the needs of the veterinary industry by providing a product that will allow animals that would normally be euthanized to return to a relatively normal life. The subcutaneous fluid dispensing method and apparatus of the present invention provides an implantable catheter tube attached to a pad or skirt for suturing to the skin of the animal. A stylet of solid material such as stainless steel is provided. This stylet runs the length of the catheter tube and is attached to the tube by a screw on luer adapter. The stylet adds rigidity to the proximal end of the tube so that the combination of catheter tube and stylet can be passed through the subcutaneous tissues via a small incision or opening made in the skin of the patient.

The tube is fenestrated with small openings so that when fluids or medications are administered they can diffuse into the subcutaneous space along the length of the tube. For the administration of subcutaneous fluids, it is preferable that not more than the distal ⅔ of the catheter tube contains fenestrations so as to avoid fluids forming around the neck of the patient or leaking through the small incision or opening where the tube penetrates the skin.

There is a silicone or other non-reactive material skirt or pad which covers the area of entrance of the tube into the skin. This skirt provides a strong but comfortable surface to be secured to the animal. This skirt or pad protects the small exposed portion of the tube from working its way out from under the skin when the animal bends its neck down. The skirt is designed in such a manner that the area where the tube enters the skin is completely covered by the skirt. It also prevents the animal from grasping the tube with a claw and pulling the assembly out of the body. However, the incision or opening is preferably made between the animal's shoulder blades and behind the skull so that the animal's ability to claw, bite or scratch at the catheter is restricted.

Another alternative method of securing the catheter is to attach a small wrap of material around the silicone such as dacron that would allow the subcutaneous tissues to grow into the catheter and hold it in place indefinitely with no attachment directly to the skin.

Another method of attachment involves securing a small silicone bulb to the tubing just distal to the location where a small skirt is located on the proximal tube. Once the tube is inserted the bulb is pulled under the skin and a suture placed to close the skin over the bulb. The tube could not migrate into the patient because of the skirt on top of the skin and could not be pulled out of the patient because of the bulb under the skin. Advantages of the alternative methods of attachment are less discomfort to the patient and maintenance for the owner or veterinarian. Surgical time would also be decreased because fewer sutures would be required.

Another component of the device is a luer female hub that seals the tube and contains a rubber diaphragm. The hub is matched to a clip on plastic injection stylet that allows its small plastic hollow probe to be inserted through the diaphragm of the hub and into the fluid tube. Prongs of the injection stylet attach to the hub to make a solid connection while the medication or fluids are being administered. The I.V. set can be connected directly to the injection stylet. Once treatment is completed the wings of the injection stylet are compressed and the and the plastic hollow probe is withdrawn and recapped to protect its sterility.

Particularly, the present invention provides an improved method of administering fluids to an animal such as a pet (cat, dog, etc.). The method includes an initial step of forming one or more openings in the animal's skin, at least one of the openings being positioned proximally on the animal's body.

An elongated catheter is provided that includes a catheter wall, a central, fluid containing lumen, and proximal and distal end portions, the distal end portion having at least one and preferably a plurality of discharge openings.

A majority of the length of the catheter is placed in a subcutaneous space that extends proximally (eg. at the neck) to distally (eg. at the flank) on the animal's body.

The method further contemplates an anchoring of the proximal portion of the catheter to the animal's skin next to the incision.

Fluids are then transmitted to the animal via the catheter by removably connecting a fluids containing vessel to the catheter and discharging the fluids from the vessel into the subcutaneous space via the catheter.

The catheter wall is preferably provided with spaced apart wall openings that are positioned along a portion of its length, and further comprising the step of discharging the fluid into the subcutaneous space via the catheter wall openings, the openings preferably being positioned at the distal portion of the catheter.

The dispensing openings are preferably not positioned at the proximal portion of the catheter so that fluid does not flow over the neck area of the animal and out of the incision or opening.

In the preferred embodiment, an opening or an incision is positioned on the animal's body at a location that restricts the animal's ability to scratch, bite at or claw at the incision or opening, or at the proximal end portion of the catheter.

In the preferred embodiment, the incision or opening is positioned on or near the dorsal neck region of the animal.

The incision or opening can be positioned on the animal's body generally in between the animal's shoulder blades, making it difficult for the animal to reach the tube either by biting or clawing.

In one embodiment, two incision or openings are formed, one proximally and one distally. In this embodiment, a pair of forceps or other instrument can be used to pull the catheter from one incision or opening to the other.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 4:
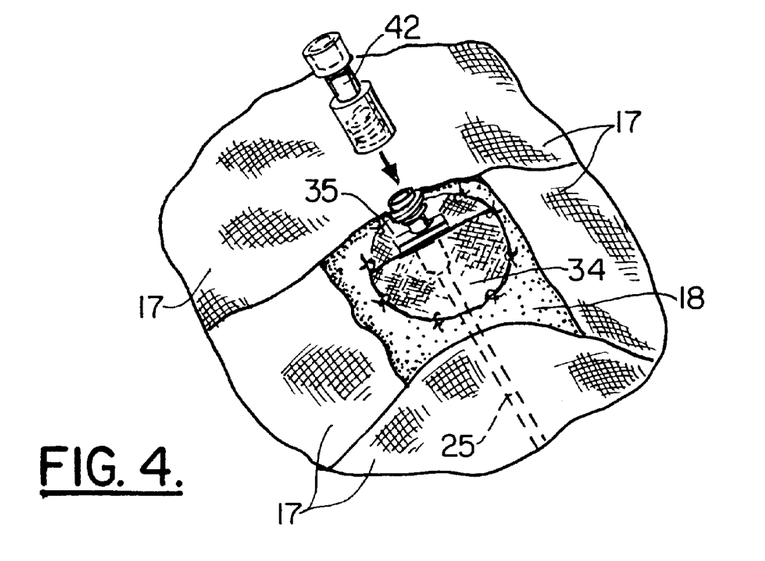
FIG. 4 is an additional method step of the preferred method of the present invention.
Figures 5, 6:
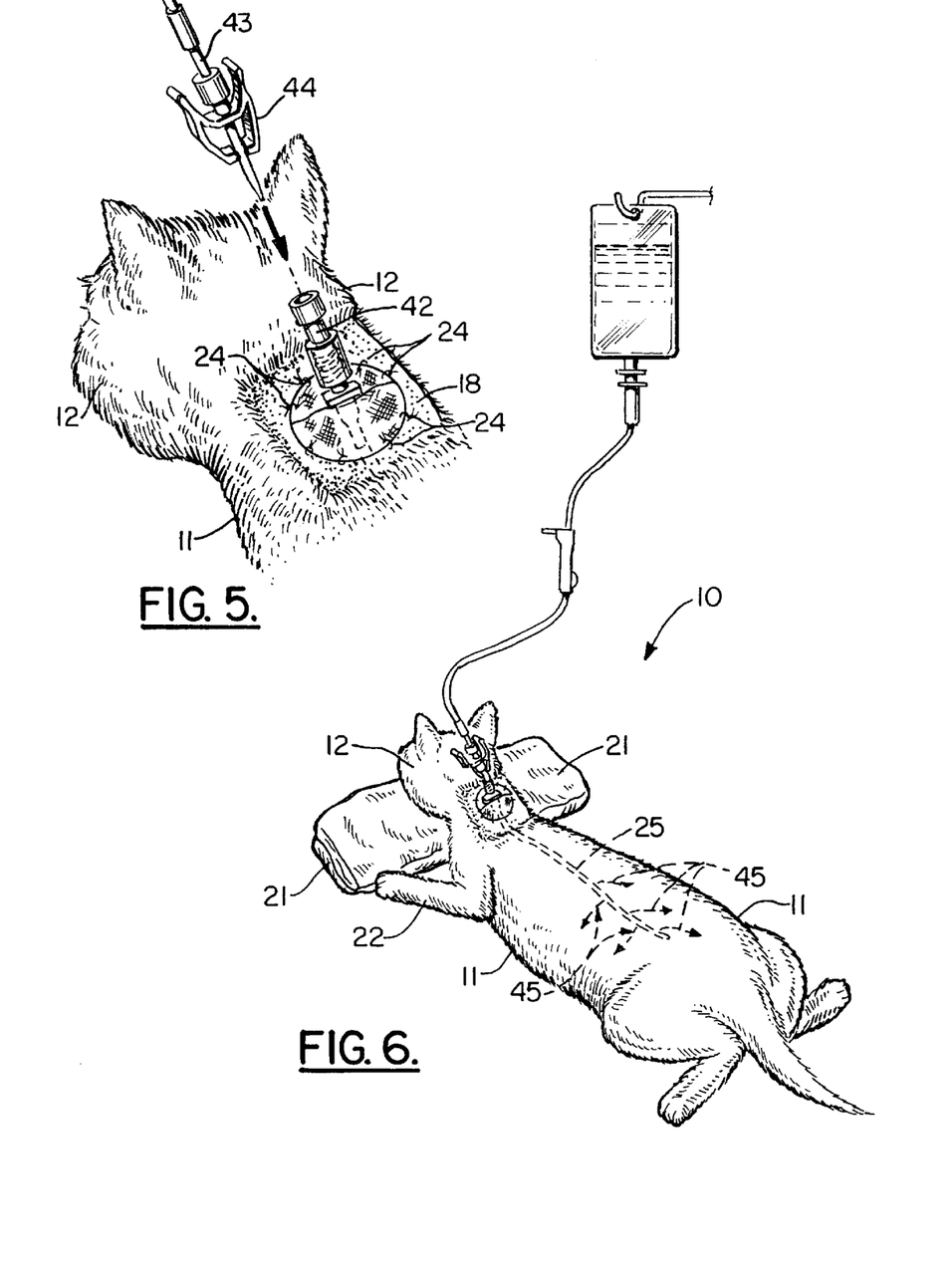
FIG. 5 is a close-up perspective view illustrating a connection of a fluids source to the catheter portion as part of the method of the present invention.
FIG. 6 is a perspective view of the preferred embodiment of the apparatus of the present invention and illustrating an additional method step of the present invention.

FIGS. 1–13 show the preferred embodiment of the apparatus of the present invention which is designated generally by the numeral 10 in FIG. 6.

Animal catheter apparatus 10 is shown during the administration of fluids to an animal body 11 such as the cat shown. It should be understood, however, that the method and apparatus of the present invention can be utilized with other animals such as research, zoo, bird and exotic animals, including dogs, etc.

Figure 1:
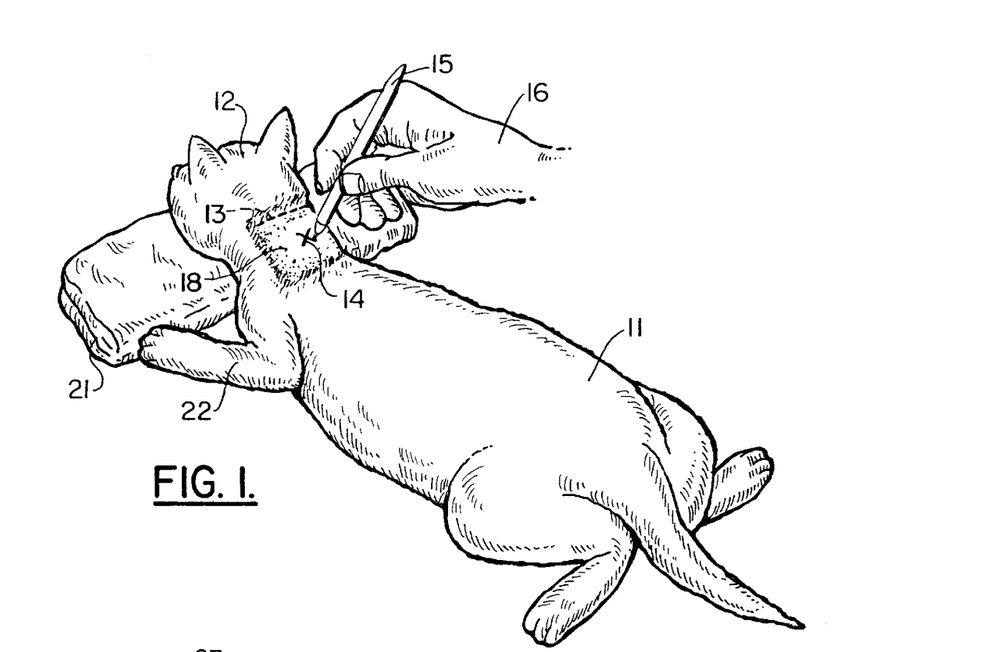
FIG. 1 is a perspective view illustrating the initial method step of the preferred method of the present invention.

In FIGS. 1–4, animal body 11 is shown illustrating the animal's head 12 and neck and wherein the veterinarian has cleared an area of the animal's skin 18 of fur. In FIG. 1, a reference line 13 has been marked at the base of the animal's skull. A reference mark 14 is first placed as shown on FIG. 1 with a suitable marker 15. The mark 14 can be about ¾"–1" from the reference line 13.

Figure 2:
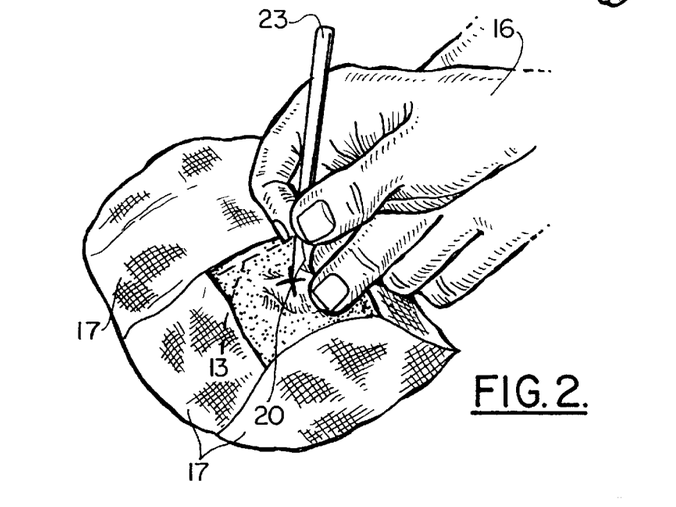
FIG. 2 is a close-up perspective view illustrating the second method step of the preferred method of the present invention.
Figure 3:
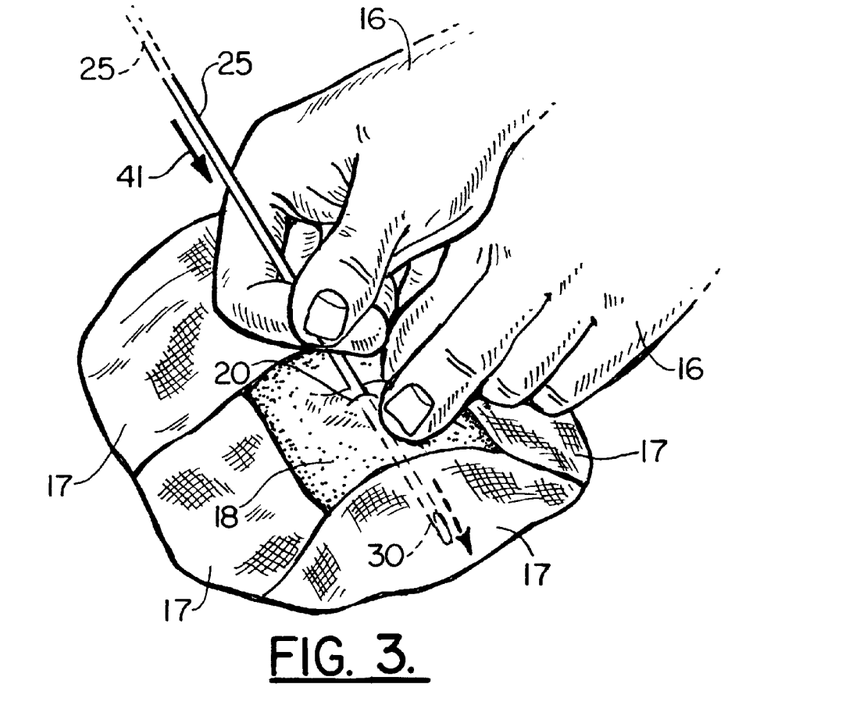
FIG. 3 is a close-up perspective view of an additional method step of the preferred method of the present invention.

The veterinarian 16 surgically drapes the animal using a plurality of drapes 17 as shown in FIGS. 2–4. The drapes 17 define an operative site 19 wherein the veterinarian 16 forms an opening or incision 20 as shown in FIG. 2, using a suitable instrument such as a scalpel, stylet or needle. During this procedure, the animal body 11 can be supported with one or more supports 21 and administered anesthesia in a manner known in the art.

In FIGS. 7–13, a catheter tube 25 is shown that includes a catheter wall 26 surrounding a central, fluid conveying lumen 27. The catheter 25 has a proximal end 28, distal end 29, and an reinforced tip 30 supported at the distal end 29 as shown in FIG. 5. As shown in FIGS. 16–17, the distal tip can alternatively provide a tip 30A having barbs 47 that grip the catheter tube wall 26 at the lumen 27. The catheter tube 25 is preferably manufactured of a material (eg. silicone) that can remain in place subcutaneously for up to one year.

Figures 7, 8, 9, 10, 11:
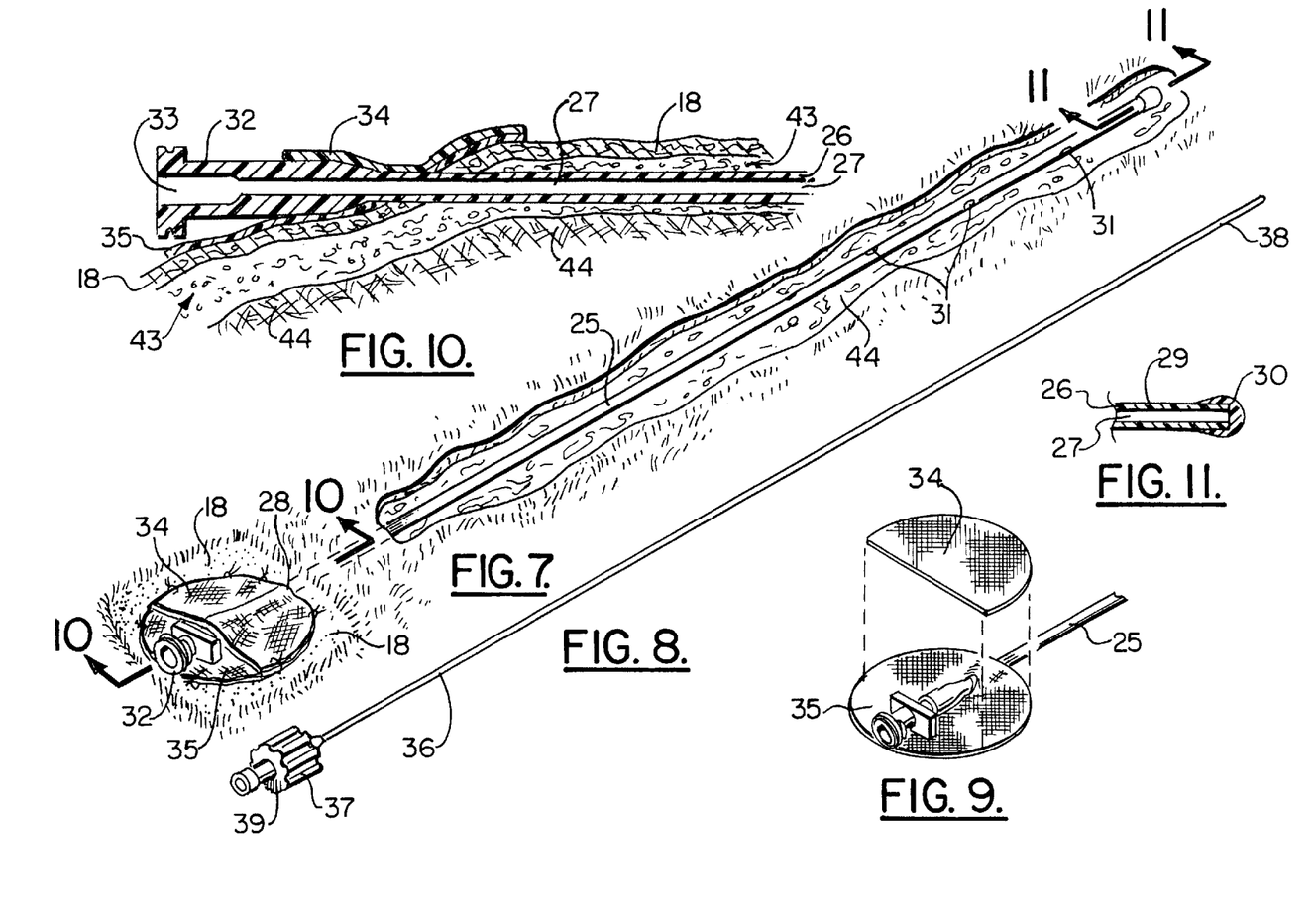
FIG. 7 is a partial perspective view of the preferred embodiment of the apparatus of the present invention illustrating the catheter portion thereof.
FIG. 8 is a partial perspective view of the preferred embodiment of the apparatus of the present invention illustrating the stylus portion thereof.
FIG. 9 is a fragmentary perspective view of the preferred embodiment of the apparatus of the present invention.
FIG. 10 is a partial sectional view of the preferred embodiment of the apparatus of the present invention taken along lines 10—10 of FIG. 7.
FIG. 11 is a fragmentary sectional view of the preferred embodiment of the apparatus of the present invention taken along lines 11—11 of FIG. 7.

This distal tip 30 assists the veterinarian during an insertion of catheter 25 and its stylus 36 into the subcutaneous 43 that is in between the animal's skin 18 and muscle tissue 44. This subcutaneous space 43 can include fatty tissue. FIG. 8 shows the stylus 36. The stylus 36 has a proximal end 37 and a distal end 38. Catheter 25 provides a plurality of openings 31 that are spaced at intervals as shown in FIG. 7. In the preferred embodiment, these openings 31 are preferably in the catheter wall 26 at the distal portion of the catheter 25 as shown. By placing the openings 31 at the distal portion of the catheter 25, fluid that is to be administered to the animal or pet does not flow out of the incision or opening.

Fitting 32 is affixed to proximal 28 end of catheter 25. Fitting 32 has an open-ended socket 33 that can be externally threaded for forming a threaded connection with fitting 39 that is at the proximal 37 end of stylus 36. In this fashion, the combination of stylus 36 and catheter 25 can be connected together as a unit, prior to the insertion step shown in FIG. 3.

In order to affix the proximal 28 end portion of catheter 25 to the animal's skin 18 at operative site 19, an upper pad 34 and a lower pad 35 define a skirt provided as shown in FIG. 9. The skirt can be used to cover the area of the entrance of the catheter tube into the animal's skin 18 at incision or opening 20. The skirt that includes pads 34, 35 is secured with sutures 24 (see FIG. 5). This skirt protects the small exposed portion of the catheter tube 25 from working its way out from under the animal's skin when the animal bends its neck, such as when it lowers its head 12.

Figures 12, 13, 16, 17:
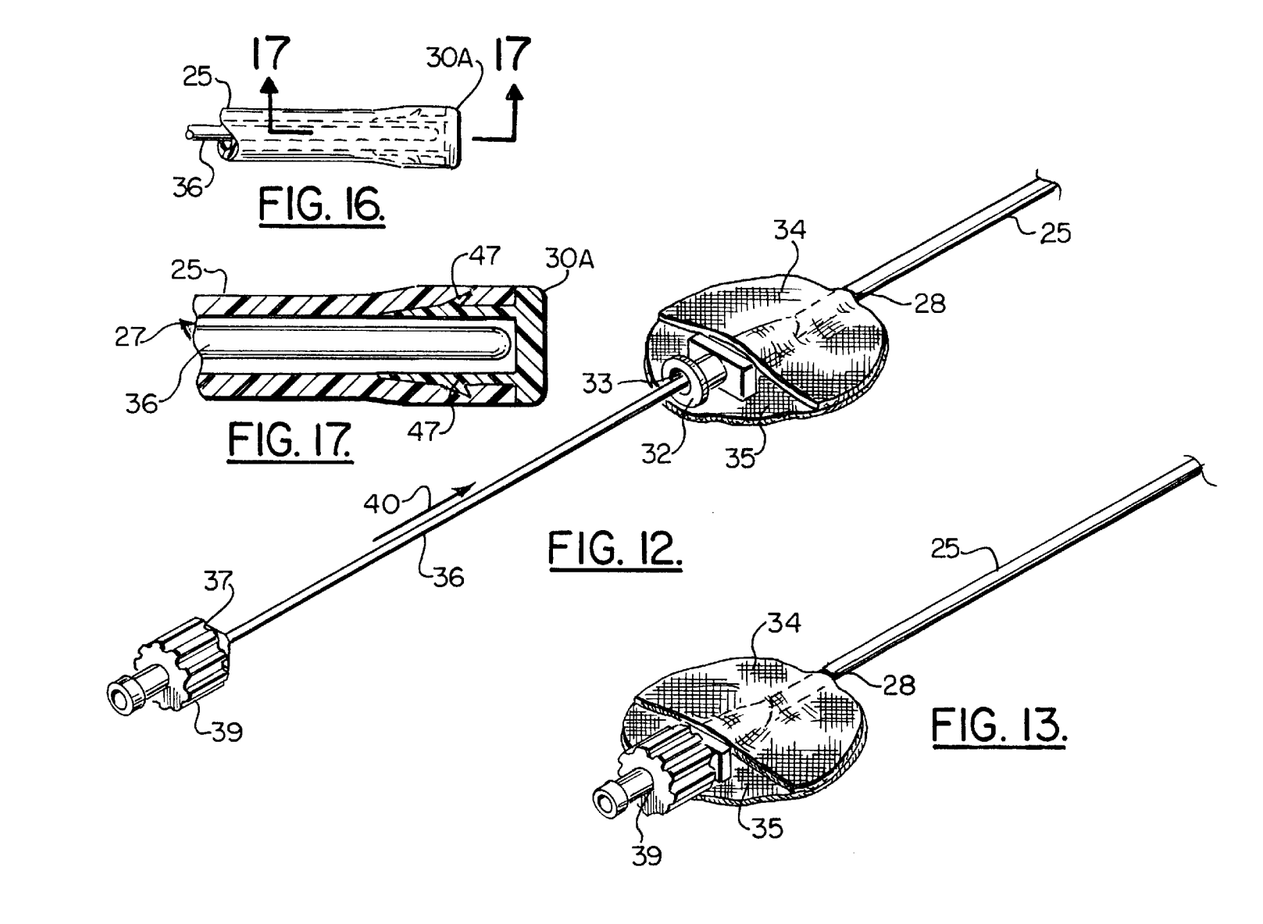
FIG. 12 is a partial perspective view of the preferred embodiment of the apparatus of the present invention.
FIG. 13 is another partial perspective view of the preferred embodiment of the apparatus of the present invention.
FIGS. 16–17 show an alternate construction for the catheter tube distal tip.

Arrow 40 in FIG. 12 illustrates the insertion of stylus 36 into the open-ended socket 33 of fitting 32 and then into the lumen 27 of catheter 25. As shown in FIG. 10, the open-ended socket 33 of fitting 32 communicates with the lumen 27 of catheter 25.

Figure 14:
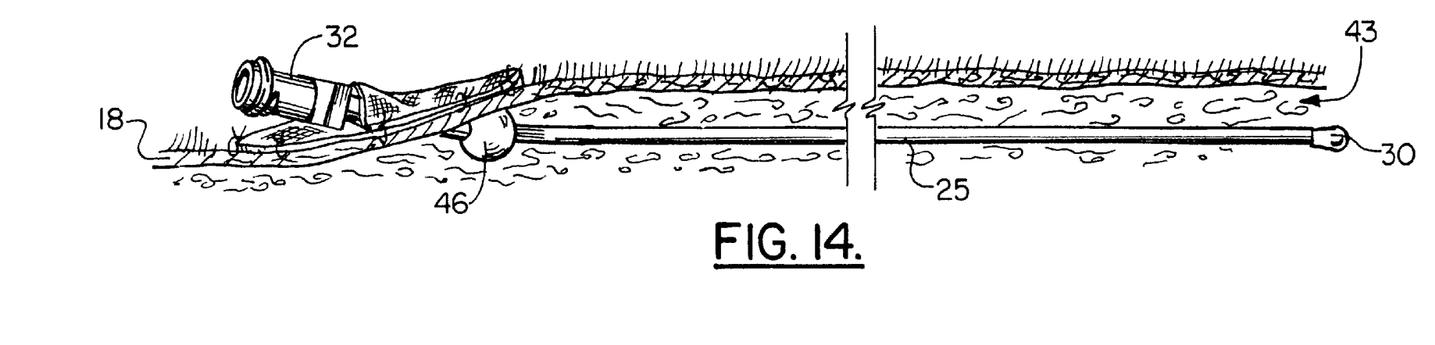
FIGS. 14–15 show alternate constructions helping to anchor the catheter portion of the apparatus at its proximal end portion.

Arrow 41 in FIG. 3 illustrates the insertion of the assembly of catheter 25 and stylus 36 through the incision or opening 20 and into the subcutaneous space 43 of the animal body 11. The catheter 25 and its stylus 36 are preferably inserted proximally, beginning at the incision or opening 20 and then distally to the position shown in phantom lines in FIG. 6. Arrows 45 in FIG. 6 schematically illustrate the flow of fluids from the lumen 27 of catheter 25 into the subcutaneous space 43 of the animal body 11. FIG. 14 shows an optional, alternate construction for catheter tube 25 that enhances the method of attachment at the proximal end portion of the catheter tube 25. This optional construction involves securing a small silicone bulb 46 to the catheter tubing 25 just distal to the location where a small skirt is located on the proximal tube end 28. In the embodiment of FIG. 14, once the catheter tube 25 is inserted, the bulb 46 is pulled under the skin 18 and a suture 24 is placed to close the skin 18 over the bulb 46. The catheter tube 25 could not migrate into the patient because of the skirt (pads 43,44) on top of the skin 18 and could not be pulled out because of the bulb 46 under the skin 18.

Figure 15:
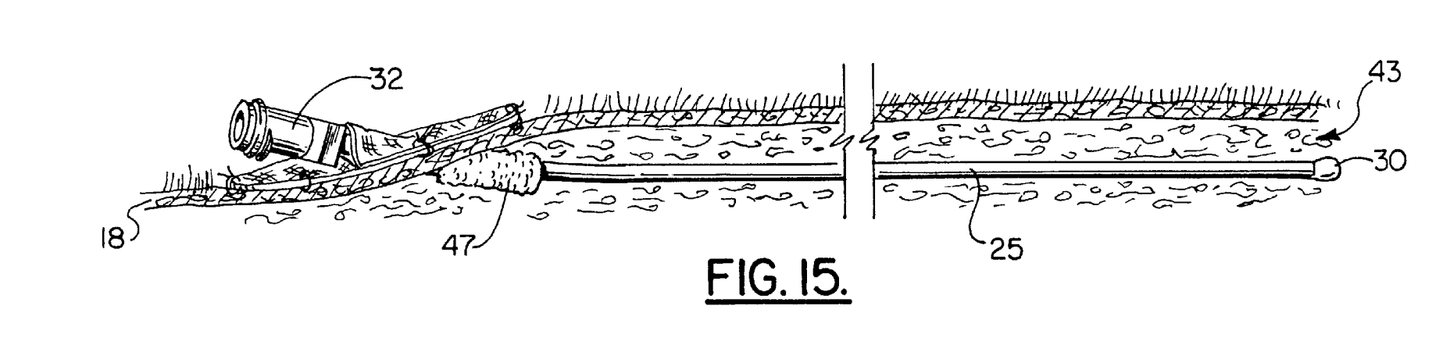

In FIG. 15, another alternative construction and method of securing the catheter tube 25 is shown. In FIG. 15, a small cuff 47 of material is wrapped around and secured to the proximal end 28 of the catheter tube 25. The cuff 47 can be of a material such as a dacron that would allow the subcutaneous tissues to cuff 47 and hold it and the catheter tube 25 in place indefinitely with no attachment directly to the skin.

A shorter stylus member such as the stylus 36 can be used to prevent bending of the catheter tube 25 proximal end 28 in between fluid injections. The shorter stylus member can be a few centimeters in length.

Advantages of the alternative constructions shown in FIGS. 14–15 and the alternate methods of attachment they provide are less discomfort to the patient and less maintenance for the owner or veterinarian. Surgical time would also be decreased because fewer sutures would be required.

The catheter tube 25 can be made of any material that is compatible over a long period of time with the animal's body, such as silicone.

PARTS LIST

The following is a list of suitable parts and materials for the various elements of the preferred embodiment of the present invention.

| | |
|---|---|
| 10 | animal catheter apparatus |
| 11 | animal body |
| 12 | head |
| 13 | reference line |
| 14 | mark |
| 15 | marker |
| 16 | veterinarian |
| 17 | surgical drape |
| 18 | animal's skin |
| 19 | operative site |
| 20 | incision or opening |
| 21 | support |
| 22 | animal's paw |
| 23 | scalpel |
| 24 | suture |
| 25 | catheter |
| 26 | catheter wall |
| 27 | lumen |
| 28 | proximal end |
| 29 | distal end |
| 30 | enlarged tip |
| 30A | enlarged insert tip |
| 31 | opening |
| 32 | fitting |
| 33 | socket |
| 34 | upper pad |
| 35 | lower pad |
| 36 | stylet |
| 37 | proximal end |
| 38 | distal end |
| 39 | fitting |
| 40 | arrow |
| 41 | arrow |
| 42 | needleless connection |
| 43 | subcutaneous space |
| 44 | muscle tissue |
| 45 | arrow |
| 46 | silicone bulb |
| 47 | barb |

The foregoing embodiments are presented by way of example only; the scope of the present invention is to be limited only by the following claims.

What is claimed is:

1. A method of administering fluids to a subcutaneous space of an animal that is suffering from chronic kidney disease, comprising the steps of:
    a) forming one or more openings in the animal's skin, at least one of the openings being positioned proximally on the animal's body;
    b) providing an elongated catheter that includes a wall, a lumen, and proximal and distal end portions, the distal end portion having at least one discharge opening;
    c) placing a majority of the length of the catheter in a subcutaneous space that extends proximally to distally on the animals body and wherein the catheter does not terminate either intravenously, intra-arterially or intra-peritoneally;
    d) anchoring the proximal portion of the catheter to the animal's skin externally and at the opening formed in step "a"; and
    e) transmitting fluids to the animal via the catheter by removably connecting a fluids containing vessel to the catheter and discharging the fluids from the vessel into the subcutaneous space via the catheter.

2. The method of claim 1 wherein in step "a" the openings are surgical incisions.

3. The method of administering fluid to an animal of claim 1 wherein the catheter wall is provided with wall openings along a portion of its length, and further comprising the step of discharging the fluids into the subcutaneous space via the catheter wall openings.

4. The method of administering fluid to an animal of claim 1 wherein the catheter wall is provided with wall openings along a portion of its length closest to the distal end portion of the catheter and further comprising the step of discharging the fluids into the subcutaneous space via the catheter wall openings.

5. The method of administering fluid to an animal of claim 1 wherein the incision or opening includes an incision or opening positioned next to the neck region of the animal.

6. The method of administering fluid to an animal of claim 1 wherein the incision or opening is positioned on the animal's body generally in between the animal's shoulder blades.

7. The method of administering fluid to an animal of claim 1 wherein the incision or opening is positioned on the animal's body at a location that restricts the animal's ability to scratch, chew or claw at the incision or opening or catheter.

8. The method of administering fluid to an animal of claim 1 wherein there are two openings formed in step "a".

9. The method of administering fluid to an animal of claim 1 wherein there are two incision or openings formed in step "a" and in step "c" the catheter is inserted through one incision or opening routed to the other incision or opening.

10. The method of administering fluid to an animal of claim 1 wherein there are two incision or openings formed in step "a" including one proximal incision or opening and one distal incision or opening, and in step "c" the catheter is inserted through the distal incision or opening routed to the proximal incision or opening.

11. A method of administering fluids to a subcutaneous space of an animal that is suffering from chronic kidney disease, comprising the steps of:
    a) forming only one opening in the animal's skin, the opening being positioned proximally on the animal's body;
    b) providing an elongated catheter that includes a wall, a lumen, and proximal and distal end portions, the distal end portion having at least one discharge opening;
    c) placing the catheter through the incision or opening and into a subcutaneous space that is within the animals body until a majority of the length of the catheter occupies the subcutaneous space and wherein the catheter does not extend intravenously, intra-arterially or intra-peritoneally;
    d) anchoring the proximal portion of the catheter to the animal's body at the incision or opening formed in step "a"; and
    e) transmitting fluids to the animal subcutaneously via the catheter.

12. The method of administering fluid to an animal of claim 11 wherein the catheter wall is provided with wall openings along a portion of its length and further comprising the step of discharging the fluids into the subcutaneous space via the catheter wall openings.

13. The method of administering fluid to an animal of claim 11 wherein the catheter wall is provided with wall openings along a portion of its length closest to the distal end portion of the catheter and further comprising the step of discharging the fluids into the subcutaneous space via the catheter wall openings.

14. The method of administering fluid to an animal of claim 11 wherein the incision or opening includes an incision or opening positioned next to the neck region of the animal.

15. The method of administering fluid to an animal of claim 11 wherein the incision or opening is positioned on the animal's skin generally in between the animal's shoulder blades.

16. The method of administering fluid to an animal of claim 11 wherein the incision or opening is positioned on the animal's skin at a location that restricts the animal's ability to scratch, chew or claw at the incision or opening.

17. The method of claim 11 wherein in step "d" the proximal end portion of the catheter is attached to the animal's skin externally of the subcutaneous space.

18. A animal catheter for dispensing fluids to an animal body that includes skin and a subcutaneous space underneath the skin, comprising:
   a) a catheter tube having a catheter wall, a lumen, and proximal and distal end portions;
   b) fitting attached to the proximal end portion of the catheter tube, the fitting having an opening that communicates with the catheter lumen;
   c) the fitting including an attachment skirt portion that enables one to anchor the catheter tube at the fitting to the animal's skin and externally of the subcutaneous space, the skirt including a sheet of material that extends radially from the catheter;
   d) only a portion of the catheter wall having wall openings therethrough, a perforated portion including at least a part of the distal end portion of the catheter tube; and
   e) a portion of the catheter tube that is proximal of the skirt having none of the perforated portion.

19. The animal catheter for dispensing fluids to an animal body of claim 18 wherein only the distal one half end portion of the catheter tube has said wall openings.

20. The animal catheter for dispensing fluids to an animal body of claim 18 wherein the proximal end portion of the catheter tube does not have any of said wall openings.

21. The animal catheter for dispensing fluids to an animal body of claim 18 wherein only the distal two thirds end portion of the catheter tube has said wall openings.

22. A method of administering fluids to a subcutaneous space of an animal that is suffering from chronic kidney disease, comprising the steps of:
   a) forming one or more openings in the animal's skin, at least one of the openings being positioned proximally on the animal's body;
   b) providing an elongated catheter that includes a wall, a lumen, and proximal and distal end portions, the proximal end portion having a skirt, the distal end portion having at least one discharge opening;
   c) placing the catheter in a subcutaneous space that extends proximally to distally on the animals body, wherein a majority of the length of the catheter is positioned in the subcutaneous space;
   d) anchoring the skirt of the catheter to the animal's skin externally and at the incision or opening formed in step "a"; and
   e) transmitting fluids to the animal via the catheter by removably connecting a fluids containing vessel to the catheter and discharging the fluids from the vessel into the subcutaneous space via the catheter.

23. The method of administering fluid to an animal of claim 22 wherein the catheter wall is provided with wall openings along a portion of its length, and further comprising the step of discharging the fluids into the subcutaneous space via the catheter wall openings.

24. The method of administering fluid to an animal of claim 22 wherein the catheter wall is provided with wall openings along a portion of its length closest to the distal end portion of the catheter and further comprising the step of discharging the fluids into the subcutaneous space via the catheter wall openings.

25. The method of administering fluid to an animal of claim 22 wherein the incision or opening includes an incision or opening positioned next to the neck region of the animal.

26. The method of administering fluid to an animal of claim 22 wherein the incision or opening is positioned on the animal's body generally in between the animal's shoulder blades.

27. The method of administering fluid to an animal of claim 22 wherein the incision or opening is positioned on the animal's body at a location that restricts the animal's ability to scratch or claw at the incision or opening.

28. The method of administering fluid to an animal of claim 22 wherein there are two incision or openings formed in step "a".

29. The method of administering fluid to an animal of claim 22 wherein there are two incision or openings formed in step "a" and in step "c" the catheter is inserted through one incision or opening routed to the other incision or opening.

30. The method of administering fluid to an animal of claim 22 wherein there are two incision or openings formed in step "a" including one proximal incision or opening and one distal incision or opening, and in step "c" the catheter is inserted through the distal incision or opening routed to the proximal incision or opening.

31. The method of claim 22 wherein in step "b" the proximal end portion of the catheter tube has a bulb and in step "d" the bulb is positioned under the animal's skin next to the incision or opening.

32. The method of claim 22 wherein in step "b" the proximal end portion of the catheter tube has a cuff of tissue ingrowth material and in step "d" the cuff tissue ingrowth material is positioned under the animal's skin next to the incision or opening.

33. The method of claim 22 wherein in step "d" the skirt is so connected to the catheter that the area where the catheter enters the skin at the opening is completely covered by the skirt, to prevent the tube from migrating out of the opening.

* * * * *